United States Patent
Baccelli et al.

(10) Patent No.: US 8,728,083 B2
(45) Date of Patent: May 20, 2014

(54) DEVICE FOR TENSIONING A FLEXIBLE BAND

(71) Applicant: Implanet, Societe Anonyme, Martillac (FR)

(72) Inventors: Christian Baccelli, Saucats (FR); Regis Le Couedic, Bordeaux (FR)

(73) Assignee: Implanet, Societe Anonyme, Martillac (FR)

( * ) Notice: Subject to any disclaimer, the term of this patent is extended or adjusted under 35 U.S.C. 154(b) by 0 days.

(21) Appl. No.: 13/906,550

(22) Filed: May 31, 2013

(65) Prior Publication Data

US 2013/0261680 A1 Oct. 3, 2013

Related U.S. Application Data

(63) Continuation of application No. PCT/FR2011/000639, filed on Dec. 6, 2011.

(30) Foreign Application Priority Data

Dec. 8, 2010 (FR) ...................................... 10 04786

(51) Int. Cl.
*A61B 17/70* (2006.01)
*A61B 17/88* (2006.01)

(52) U.S. Cl.
CPC ......... *A61B 17/7083* (2013.01); *A61B 17/8869* (2013.01); *A61B 17/7074* (2013.01)
USPC ...................................................... 606/86 A

(58) Field of Classification Search
CPC ........... A61B 17/7083; A61B 17/8869; A61B 17/7074
USPC .................................... 606/74, 99, 103, 86 A
See application file for complete search history.

(56) References Cited

U.S. PATENT DOCUMENTS

| 1,346,940 | A | * | 7/1920 | Collins ....................... 606/86 R |
| 6,146,386 | A | | 11/2000 | Blackman et al. |
| 8,128,635 | B2 | | 3/2012 | Belliard et al. |
| 8,162,946 | B2 | | 4/2012 | Baccelli et al. |

FOREIGN PATENT DOCUMENTS

WO 2007/034112 3/2007

OTHER PUBLICATIONS

International Search Report mailed Apr. 4, 2012 in corresponding International Application No. PCT/FR2011/000639.

* cited by examiner

*Primary Examiner* — Ellen C Hammond
(74) *Attorney, Agent, or Firm* — Banner & Witcoff, Ltd.

(57) ABSTRACT

A device (17) is provided for tensioning a flexible band (3) used to maintain a bone element on an implant. The device includes a rod (18) having a first end (19) provided with means (20) for bearing on the implant, a movable part (32) for hooking the flexible band onto a portion (28) of the device, and means (34) for adjustably locking the movable part in translation in relation to the portion of the device. The rod (18) includes a gripping handle (26) at the second end (27) thereof. The aforementioned portion of the device forms an angle α with the rod (18) to which it is rigidly connected at an intermediary point, the direction of the band being altered at an angle, and the aforementioned adjustable locking means (34) includes manual screwing means (35) for actuating the movable part.

18 Claims, 4 Drawing Sheets

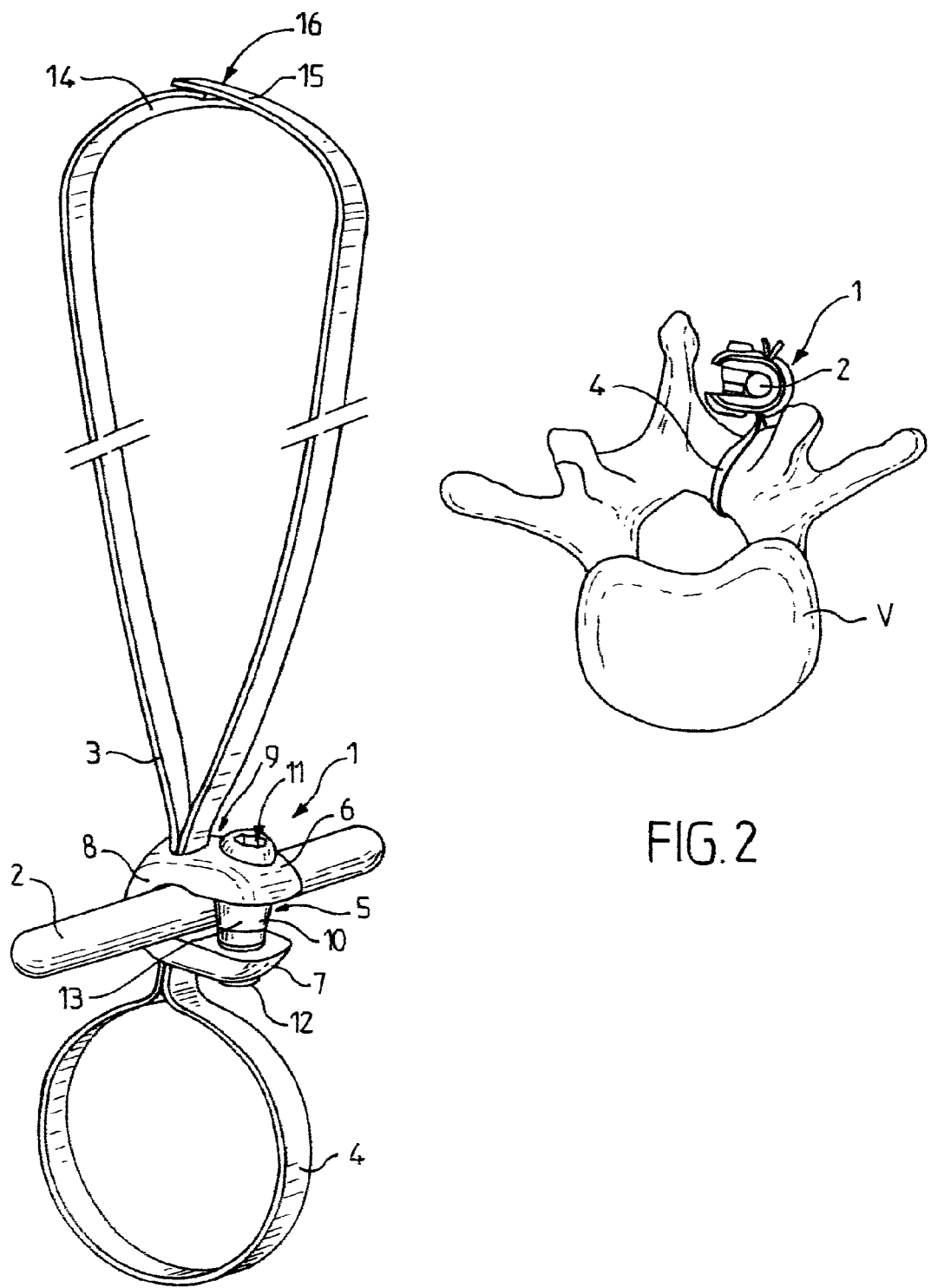

DEVICE FOR TENSIONING A FLEXIBLE BAND

CROSS REFERENCE TO RELATED APPLICATION

This application is a continuation of co-pending International Application No. PCT/FR2011/000639, filed Dec. 6, 2011, the contents of which are hereby incorporated by reference in their entirety.

BACKGROUND OF THE INVENTION

The present invention relates to a device for tensioning a flexible strip for securing a bony element to an implant, comprising a rod having a first end provided with means for bearing on the implant, a mobile part for attaching the flexible strip to a portion of the device and adjustable means for blocking the part that is mobile in translation relative to said portion of the device.

It is particularly importantly applicable, although not exclusively applicable, to the field of the straightening of the spinal column of a patient having abnormal curvature.

In this case, with the vertebrae not being correctly aligned relative to one another in relation to the vertebral axis, they exhibit mutual inclinations.

In order to straighten the assembly, it is known to reset the lateral edges of the vertebrae to a substantially equivalent distance, on all sides of the spinal column, by the use of rods linking together either are screws, that are inserted into the vertebrae themselves, or hooks that are introduced along the vertebral canal.

However, such devices present drawbacks because they are aggressive.

To mitigate these drawbacks, there has been proposed a flexible link for fixing the vertebra to the link part which is in turn fixed to the straightening rod.

Means for blocking the flexible link by reclosing the link part on the rod are then necessary.

The problem that the invention seeks to resolve is in this case that of the tensioning of this flexible link for fixing the vertebra to the link part.

In practice, it is important for the user, when fitting this link, to be able to gradually retighten the latter without in any way damaging the bony element which is then compressed by the flexible strip.

There are currently tensioning ancillaries provided with a rod, a part that is mobile in translation along the rod and an element mounted on the mobile part tending horizontally to separate the end of the rod from the part.

Such an ancillary does, however, present drawbacks.

It in fact entails pulling in the extension of the link itself which has to be twisted to be able to allow it to be tensioned.

Furthermore, no manual feedback of the tension is possible with such an instrument which thus requires, to avoid crushing the bony element, an adjustable dynamometric system making it possible to stop the tensioning beyond a certain determined value.

SUMMARY OF SELECTED INVENTIVE ASPECTS

The present invention aims to provide a device for tensioning a flexible band that provides a better response than those previously known to the requirements of the practice, notably in that it will allow for a much greater flexibility, a better sensitivity to the degree of tensioning because of the very design of the tools used for such a tensioning, and in that it presents much improved and simple adjustment possibilities.

To this end, in an aspect, the invention notably proposes a device for tensioning a flexible strip for securing a bony element to an implant, comprising a rod having a first end provided with means for bearing on the implant, a mobile part for attaching the flexible strip to a portion of the device and adjustable means for blocking the part that is mobile in translation relative to said portion of the device, characterized in that the rod comprises a gripping sleeve at its second end, in that said portion of the device forms an angle with the rod to which it is rigidly fixed at an intermediate level with angular return of the strip and in that the adjustable blocking means comprise manual screwing means specifically for actuating the mobile part.

The manual screwing means for actuating the mobile part which is itself offset on a lateral branch forming an angle, allow for a gradual and controlled tensioning of the flexible strip.

In advantageous embodiments, there is also recourse to one and/or other of the following arrangements:

- the adjustable blocking means comprise a rack securely attached to the portion of the device, and the screwing means comprise a non-return ratchet system with actuation key securely attached to the mobile part.
- The actuation key allows for a good manual tightening sensitivity;
- the ratchet system comprises a lever arm for releasing the ratchet. It is therefore very easy to release the tension, for example to allow for a new adjustment;
- the screwing means comprise at least one wing screw;
- the device comprises a link part between rod and device portion formed by a block provided with two sprocket wheels with mutually parallel axes for angular return of said strip in its plane, said block being securely attached to said rod;
- the link part is mobile along the rod;
- the attachment of the strip to the mobile part comprises a sprocket wheel of axis parallel to those of the sprocket wheels of the block;
- the angle of said portion of the device relative to the rod is adjustable;
- the angle α of said portion of the device relative to the rod is between 90° and 130°;
- the angle α of said portion of the device relative to the rod is 90°.

BRIEF DESCRIPTION OF THE DRAWINGS

The invention will be better understood from reading the following description of an embodiment given as a nonlimiting example. The description refers to the accompanying drawings in which:

FIG. 1 is a perspective view of the flexible strip for securing a bony element to an implant by the use of a fixing body on said implant.

FIG. 2 is a bottom view of a vertebra showing the fixing body on the rod and the flexible strip for linking the vertebra with the fixing body.

DETAILED DESCRIPTION OF EXAMPLE EMBODIMENTS

Figure 3:
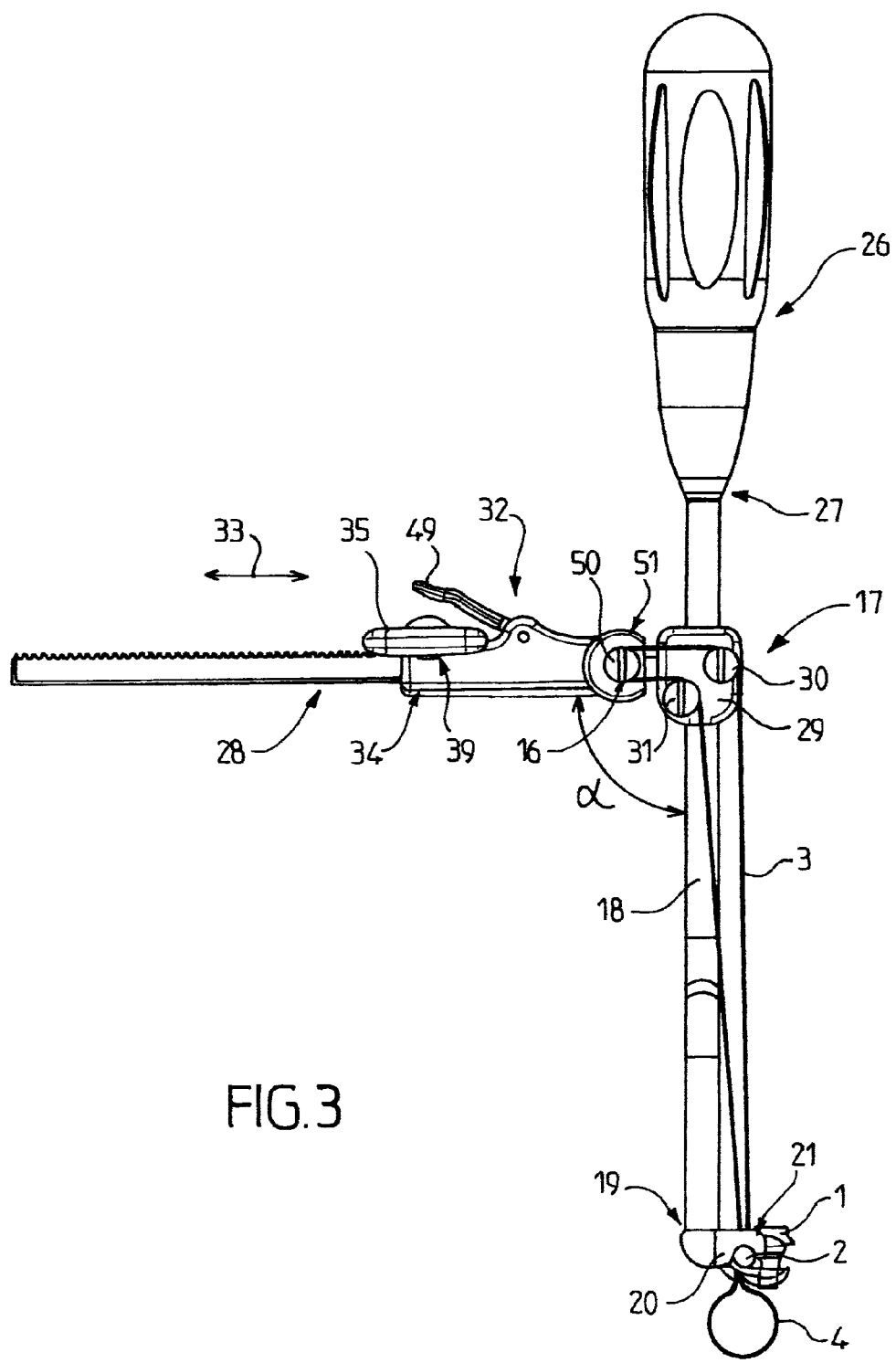
FIG. 3 is a side view of the device according to the embodiment of the invention which is more particularly described here.

Hereinafter in the description, the same reference numbers will be used to designate the same elements.

FIG. 1 shows an embodiment of a fixing body 1 on a cylindrical rod 2 and a flexible strip 3 made of braided polymer, for example polyester, 6 mm wide and 30 cm long to form the loop 4.

Adjustable means 5 for blocking the flexible strip on the fixing body 3 are provided. The fixing body 1 is, for example, formed by a part which is all one piece forming a clamp having U-shaped cross section, said U comprising two thick branches 6, 7 with a substantially demi-oval shaped cross section, symmetrical relative to a longitudinal plane and linked together by a link part 8 in the form of a half toroidal ring forming, on one side, the demicylindrical bottom of the U and, on the other side, the rounded outer walls of the branches 6 and 7.

The bottom wall of the U is of a shape complementing that of the rod 2, or substantially complementing same.

Each branch 6, 7 includes a void 9, for example in the form of a wide slot, for example five to six times wider than the thickness of the braid to facilitate its introduction during the operation.

Each branch 6 and 7 includes a cylindrical orifice for the passage of the blocking means 5, namely a bore of diameter D and a tapped cylindrical orifice for screwing of diameter d<D.

The blocking means 5 are formed by a link part 10, or screw, provided on one side with a head 11 for passing into the bore of the U and on the other side an end 12 for screwing into said facing tapped cylindrical orifice.

In the embodiment that is more particularly described here, the head of the screw 11 comprises a top cylindrical part and a bottom downwardly-tapering part 13, arranged to compress the rod 2 as the part is screwed.

The flexible strip 3 is joined at its other ends 14 and 15 at 16 for example by stitching, gluing or other means that are known per se.

FIG. 2 shows the vertebra V as fixed via the loop 4 to the rod 2 via the body 1 to allow for the tensioning of the loop 4 on the bone V as represented in FIG. 2.

Figure 4:
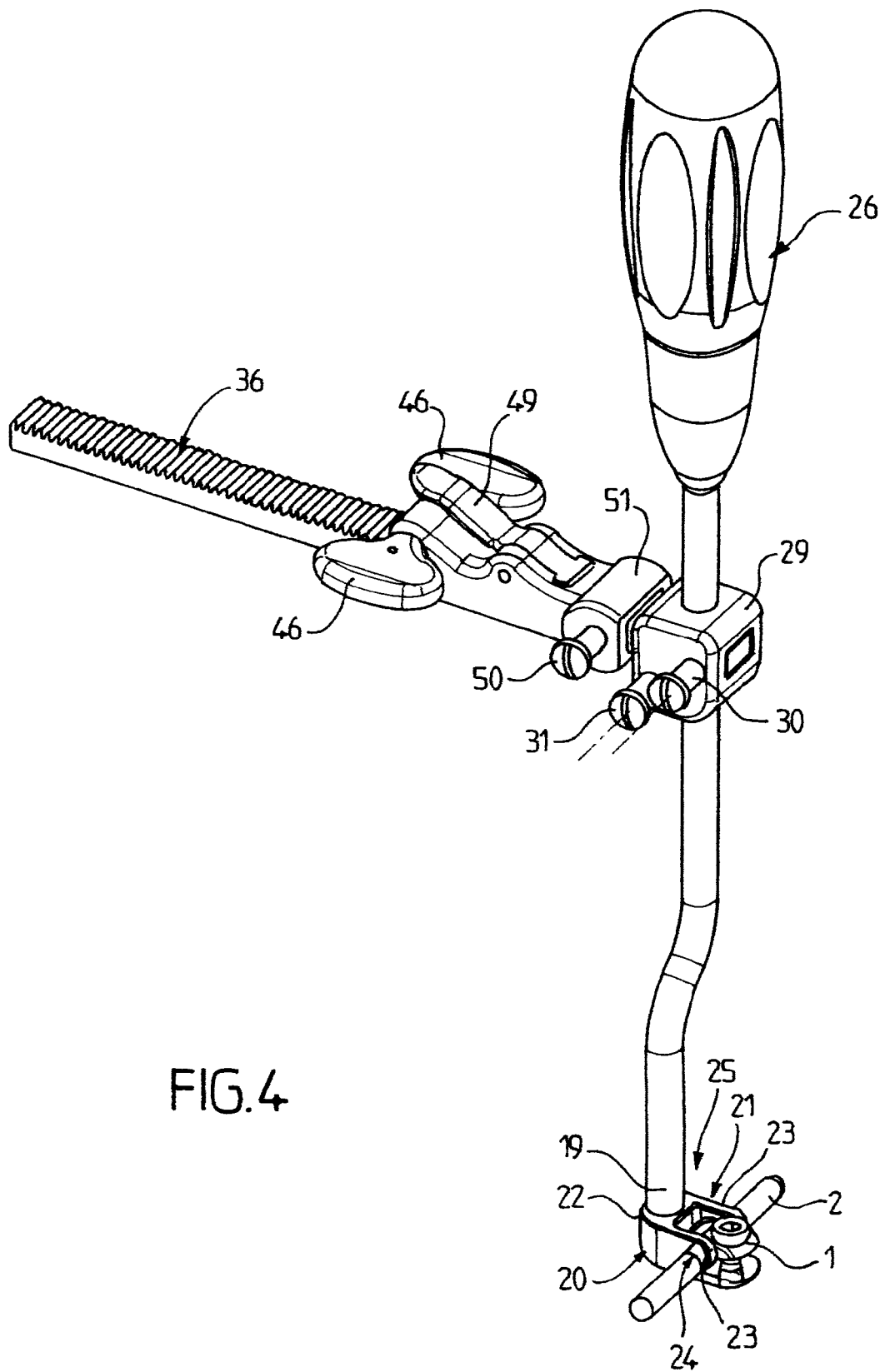
FIG. 4 is an axionometric perspective view of the device of FIG. 3.

There now follows a description of the device 17 with reference to FIGS. 3 and 4.

The device 17 for tensioning the flexible strip 3 via the loop 4 therefore comprises a slender rod 18 that is for example 40 cm long and cylindrical, provided at a first end 19 with bearing means 20 consisting, for example, of a part securely attached to the end 19 having a part 21 in the form of cylindrical hooks, of a shape complementing and arranged to cooperate with the bar 2.

More specifically, the part 20 is, for example, formed by a heel part 22 securely attached to the end 19 extended on each side by two parallel symmetrical branches 23 provided at their ends with two shoulder parts 24 arranged to cooperate with the rod 2.

The two branches 23 are themselves separated by an opening 25 into which is inserted the body 1 for fixing to the bar in a manner that is known per se.

The device includes a manual gripping sleeve 26 in the extension of the rod 18 at its second end 27.

The device according to the embodiment of the invention that is more particularly described here also includes a portion 28 forming an angle α with the rod 18 to which it is rigidly fixed at an intermediate level via a link part 29 between rod and said portion, formed by a block that is, for example, substantially parallelepipedal, provided with two sprocket wheels 30 and 31 with mutually parallel axes, perpendicular to the axis of the rod 18, for angular return of the strip 3 in its plane, towards the rod portion 28.

There is provided a part 32 that is mobile in translation (arrow 33) relative to the portion 28.

This mobile part 32 comprises adjustable means 34 for blocking the mobile part in its said translation, provided with screwing means 35.

Figure 5:
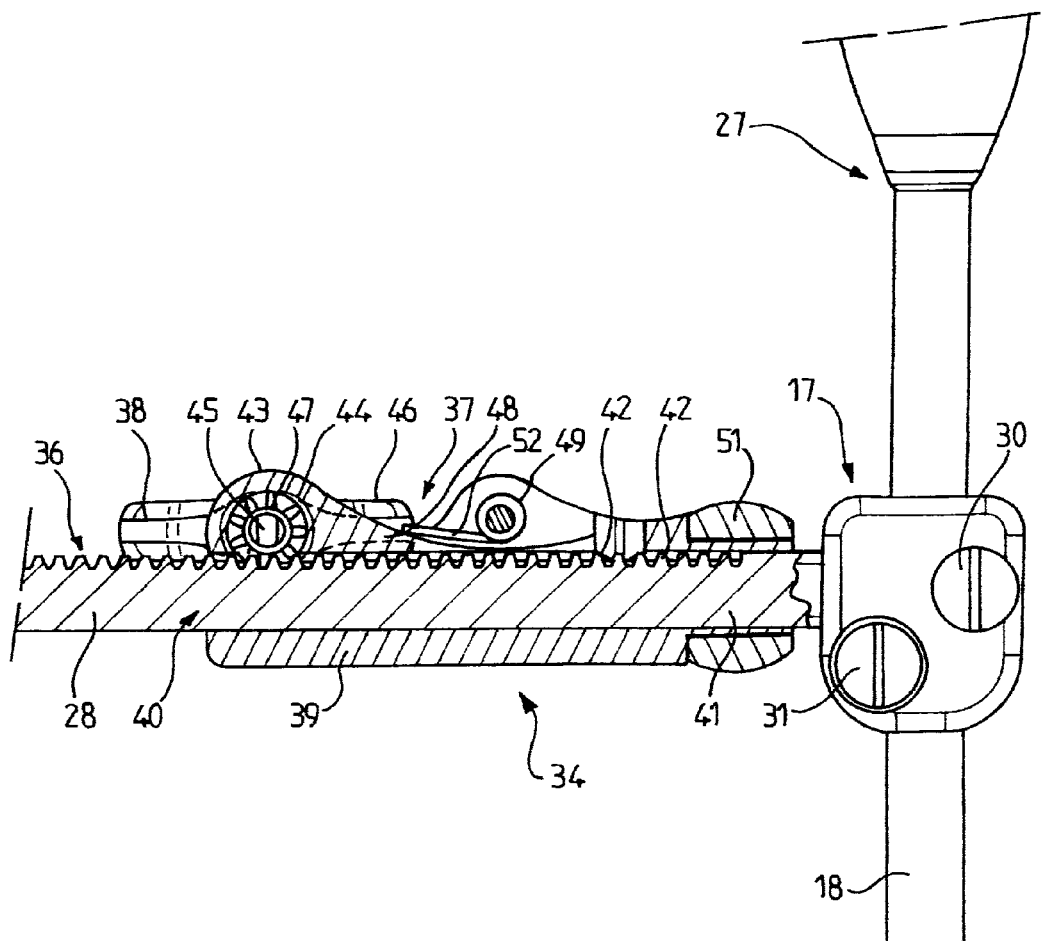
FIG. 5 is a cross-sectional view of the mobile part and of the adjustable blocking means according to the embodiment of the invention which is more particularly described here.

Referring also to FIG. 5, the adjustable blocking means 34 comprise a rack 36 securely attached to the portion 28, the screwing means 35 comprising a non-return ratchet system 37 with actuation key 38 securely attached to the mobile part.

More specifically, the adjustable blocking means comprise a body 39 pierced with a bore 40 through which passes the end 41 of the portion 28 which is fixed to the rod 18 by the link part 29.

The end 41 which includes on its top part the teeth 42 of the rack will cooperate by soft friction with the bore 40 of the part 39 which includes, in its top part, a snug 43 pierced with a lateral bore 44 through which passes the axis 45 of the wings 46 for manually actuating a toothed wheel 47 arranged to cooperate with the teeth 42 of the rack 36 so that, when the wing screws are turned, the mobile part 39 will be displaced transversely along the rod.

Ratchet means 48, known per se, are designed to be able to be actuated and unlocked when the non-return lever 49 is lifted, in a manner that is known per se.

This makes it possible in practice to release the ratchet and to release the tension of the flexible strip as will now be described in more detail.

In practice, the flexible strip, more precisely the ends of this flexible strip abutting at 16 are securely attached to a third sprocket wheel 50 fixed to the end 51 of the mobile part, so that, when the mobile part is displaced towards the outside of the rod, the strip 3 and the loop 4 are tensioned.

In an advantageous embodiment, the angle α between the portion and the rod is adjustable to be blocked in a manner that is known per se.

There now follows a description, with reference to FIGS. 2 and 3, of the operation of a device according to the invention.

The user will first of all form the loop 4 around the bony element then slide the ends of this loop through the body 1 which will then be fixed to the rod by closing the U of the part 1 via the fixing means 5 so that the branches of the flexible strip can then be slid through the orifices of the body 8.

The flexible strip is then joined at 16 at its ends by a closure system that is known per se and is then passed into the return sprocket wheels or capstans 30, 31 and 50.

The dimensioning of the flexible strip will have been calculated beforehand so that the strip is almost in the tautened position. Should the tension be greater, it is also possible to move, for example, in one embodiment, the part for fixing the portion 28 to said rod so as to obtain the desired initial tension.

The tensioning is then effected by turning the wings 46, which drives the toothed wheel 47 which meshes with the rack.

The non-return function is provided by the lever which bears with the aid of a screw 52 on the teeth of the same rack.

The tension can be released by acting on the lever 49 in order to allow for a return of the mobile part or carriage.

As is evident, and as also results from the foregoing, the present invention is not limited to the embodiments that are more particularly described. On the contrary, it encompasses all the variants therefor and notably those in which there is only a single wing key, that in which the screwing means are different and/or those in which the intermediate parts 29, 51 are formed differently.

The invention claimed is:

1. A device for tensioning a flexible strip for securing a bony element to an implant, comprising: a rod having a first end provided with means for bearing on the implant; and
   a mobile part moveable in translation along a portion of the device and a blocking device for blocking the mobile part in different translational positions on said portion of the device;
   wherein, the device comprises a grip in spaced relation to said portion of the device, said portion of the device forms an angle with the rod to which it is rigidly fixed to provide an angular return of the strip along said portion of the device, and the blocking device comprises a manually turnable mechanism for actuating movement of the mobile part along said portion of the device.

2. A device according to claim 1, wherein the blocking device comprises a rack securely attached to the portion of the device, and the manually turnable mechanism comprises a non-return ratchet system.

3. A device according to claim 2, wherein the ratchet system comprises a lever arm for releasing the ratchet.

4. A device according to claim 1, wherein the manually turnable mechanism comprises at least one wing member.

5. A device according to claim 1, further comprising a link part between the rod and the portion of the device, said link part being formed by a block provided with two wheels with mutually parallel axes for angular return of said strip along said portion of the device, said block being securely attached to said rod.

6. A device according to claim 5, wherein the link part is moveable along the rod.

7. A device according to claim 6, wherein the mobile part further comprises a wheel having its axis parallel to those of the wheels of the block, for attachment of said strip.

8. A device according to claim 5, wherein the mobile part further comprises a wheel having its axis parallel to those of the wheels of the block, for attachment of said strip.

9. A device according to claim 1, wherein an angle α of said portion of the device relative to the rod is adjustable.

10. A device according to claim 1, wherein an angle α of said portion of the device relative to the rod is between 90° and 130°.

11. A device according to claim 10, wherein the angle α of said portion of the device relative to the rod is 90°.

12. A device according to claim 1, wherein said grip is provided separate from said manually turnable mechanism.

13. A device according to claim 12, wherein said grip is connected at a second end of said rod opposite said first end.

14. A device according to claim 1, wherein said manually turnable mechanism comprises a toothed wheel rotatably engaged with a rack affixed to said portion of the device.

15. A device according to claim 1, wherein said portion of the device is rigidly affixed at an intermediate level to said rod.

16. A device for tensioning a flexible strip for securing a bony element to an implant, comprising: a rod having a first end provided with means for bearing on the implant; and
   a mobile part moveable in translation along a portion of the device and a blocking device for blocking the mobile part on said portion of the device;
   wherein, the device comprises a grip in spaced relation to said portion of the device, said portion of the device forms an angle with the rod to which it is rigidly fixed to provide an angular return of the strip along said portion of the device, and the blocking device comprises a rack securely attached to the portion of the device, and a manually turnable mechanism for actuating movement of the mobile part along said portion of the device, said manually turnable mechanism comprising a non-return ratchet system.

17. A device according to claim 16, wherein the ratchet system comprises a lever arm for releasing the ratchet.

18. A device for tensioning a flexible strip for securing a bony element to an implant, comprising: a rod having a first end provided with means for bearing on the implant; and
   a mobile part moveable in translation along a portion of the device and a blocking device for blocking the mobile part on said portion of the device;
   wherein, the device comprises a grip in spaced relation to said portion of the device, said portion of the device forms an angle with the rod to which it is rigidly fixed to provide an angular return of the strip along said portion of the device, and the blocking device comprises a manually turnable mechanism for actuating movement of the mobile part along said portion of the device, said manually turnable mechanism comprising a toothed wheel rotatably engaged with a rack affixed to said portion of the device.

* * * * *